United States Patent [19]

Heinsohn

[11] Patent Number: 5,126,478
[45] Date of Patent: Jun. 30, 1992

[54] MULTI-STAGE PROCESS WITH ADIABATIC REACTORS FOR PREPARING ALKYL GLYOXYLATES

[75] Inventor: George E. Heinsohn, Elkton, Md.

[73] Assignee: E. I. Du Pont de Nemours and Company, Wilmington, Del.

[21] Appl. No.: 417,653

[22] Filed: Oct. 4, 1989

[51] Int. Cl.$^5$ .................... C07C 69/66; C07C 69/67
[52] U.S. Cl. .................................................. 560/177
[58] Field of Search ......................................... 560/177

[56] References Cited

U.S. PATENT DOCUMENTS 4,340,748  7/1982  Baltes et al. ................ 560/177
4,820,285  4/1989  Cova et al. ................. 560/177

*Primary Examiner*—Jose G. Dees
*Assistant Examiner*—B. Frazier
*Attorney, Agent, or Firm*—Charles E. Krukiel

[57] ABSTRACT

The process in which alkyl glyoxylates are prepared by the catalytic oxidative dehydrogenation of the corresponding alkyl glycolates is improved by carrying out the process in at least two adiabatic reaction stages in series, in which no more than about 60 percent of the stoichiometric amount of oxygen is used in the first stage.

21 Claims, No Drawings

MULTI-STAGE PROCESS WITH ADIABATIC REACTORS FOR PREPARING ALKYL GLYOXYLATES

BACKGROUND OF THE INVENTION

The present invention provides an improved process for the preparation of alkyl glyoxylates by the oxidative dehydrogenation of the corresponding alkyl glycolate.

U.S. Pat. No. 1,614,195 and European Patent No. 0149439 disclose processes involving the gas phase reaction of alkyl glycolates with an oxygen source in the presence of a catalyst. A suitable oxygen source for oxidizing the alkyl glycolate is air. A number of catalysts may be used to promote the reaction. European Patent No. 0149439 discloses carrying out the reaction in the presence of a metallic silver catalyst at temperatures ranging between 325°–685° C. The details of this reaction, including the reactants and other process conditions are provided in European Patent No. 0149439.

The oxidative dehydrogenation of alkyl glycolates is strongly exothermic, resulting in temperatures in excess of 700° C. if air is used as the oxygen source unless measures are taken to limit the reaction temperature. Temperatures greater than 700° C. are known to decompose the reaction constituents. Also, high temperatures and the presence of metallic materials that catalyze undesirable reactions are the major factors contributing to a reduction in yield. Thus far, temperature control in these exothermic reactions has been achieved either by removal of heat through the wall of the reactor, by dilution of the reactant stream with a large volume of an inert substance, e.g., nitrogen, to provide additional heat capacity, or by conveying the reactants at such a high velocity through the reactor that contact time at the high temperature is minimized.

Each of these techniques for controlling temperature has certain drawbacks. Where the temperature is controlled by the removal of heat through the reactor walls, it has been necessary to use small reactors with a high ratio of surface area to volume to effect sufficient heat transfer through the reactor wall. This makes large-scale operations economically impractical. Most of the early laboratory processes in the prior art utilize this concept. For example, the reactor described in U.S. Pat. No. 1,614,195 is a tube having an inside diameter of from 2–4 cm and a length of 10M. This reactor controls the temperature of the reaction by means of heat losses through the wall of the reactor. Small diameter reactors of this type, which are designed for cooling, i.e., having a relative large surface area/volume, are expensive, especially where a relatively large throughput or production is required.

Where the temperature is controlled by dilution of the reactant stream, the resultant large volumes of the dilute reactant stream must be handled with the consequent penalty in large equipment size and lower catalyst effectiveness. Also, isolation of the desired glyoxylate from the dilute process stream is more difficult and expensive. For example, U.S. Pat. No. 4,340,748 discloses as the preferred embodiment using from 40–60 moles of nitrogen carrier gas/mole of glycolic acid ester to dilute the reaction mixture and carry away the heat of reaction. The use of such large volumes of inert gas which serve as a heat sink presents additional problems in handling of large volumes of gases and the separation of the gaseous reaction mixture from the inert gases. Further, catalyst productivity, measured as space/time yield, is low due to the high degree of dilution.

Where the temperature is controlled by using very high velocities through the catalyst bed, the pressure drop through the catalyst bed becomes excessive, necessitating the use of large equipment. Another disadvantage is that with the short contact time, a high conversion of the alkyl glycolate is not obtained; consequently, isolation of the desired product from unreacted starting material becomes more difficult. For example, European Patent No. 149,439 teaches a method of producing alkyl glyoxylates in which extremely high gas velocities and corresponding short contact times are employed. This procedure limits the conversion of the glycolate to less than 70 percent, causes a high pressure drop in the reactor, and downstream difficulties in separating product from unreacted starting material.

The prior art processes for the preparation of alkyl glyoxylates by the catalytic dehydrogenation of alkyl glycolates use a single reactor. U.S. Pat. No. 4,537,726 discloses a method for the preparation of isocyanates by reacting formamides with an oxygen-containing gas in the presence of silver or silver combination catalyst in at least two essentially adiabatic reactors in series. The technology of U.S. Pat. No. 4,537,726 cannot be translated to the oxidative dehydrogenation of alkyl glycolates due to the difference in the reactions.

U.S. Pat. No. 4,343,954 discloses the use of a two-stage adiabatic reactor system for production of formaldehyde, in which one reactor contains a silver catalyst and the other, a metal oxide catalyst. The effluent from the first reactor is cooled and fed to a second adiabatic reactor through a metal oxide catalyst bed. The conversion of methanol to formaldehyde over a silver catalyst by two separate and simultaneous pathways is detailed in *Kirk-Othmer Encyclopedia of Chemical Technology* (3rd ed., Vol. 11, p. 237). The oxidative dehydrogenation leading to formaldehyde is strongly exothermic and would result in very high temperatures if it were the only process involved. However, a parallel dehydrogenation pathway to formaldehyde is strongly endothermic and provides an internal heat sink to lower the temperature inside the reactor.

The technology of U.S. Pat. No. 4,343,954 cannot be translated to the oxidative dehydrogenation of alkyl glycolates, since the endothermic dehydrogenation pathway is unimportant in this case, accounting for less than 10 percent of the glyoxylate formed. Since the concurrent endothermic reaction is less prevalent in the alkyl glyoxylate reaction, the temperature during the oxidative dehydrogenation reaction would become excessive if the technology of U.S. Pat. No. 4,343,954 were practiced. Furthermore, the glyoxylate product possesses a second carbonyl group adjacent to the aldehyde function and, consequently, is less stable than formaldehyde. Excessive temperatures cause the glyoxylate to release one of the two adjacent carboxyl groups as a mole of carbon monoxide.

OBJECTS OF THE INVENTION

An object of the invention is to provide a process for the preparation of alkyl glyoxylates by the oxidative dehydrogenation of alkyl glycolates, in which the reaction temperature can be controlled without the attendant disadvantages described above. Another object is to provide a method for improving the selectivity of the reaction. Other objects will be apparent to those skilled in the art to which this invention pertains.

SUMMARY OF THE INVENTION

In one aspect, the present invention is a process for increasing the selectivity of a catalyzed gas phase oxidative dehydrogenation of an alkyl glycolate to an alkyl glyoxylate in which a continuous stream of a homogenous gaseous mixture of the alkyl glycolate and oxygen is contacted with an oxidation catalyst at a temperature effective to initiate the oxidation, which comprises:

(a) conducting the oxidative dehydrogenation initially in a first reaction zone in the presence of a stoichiometrically deficient amount of oxygen to limit the reaction temperature to <700° C.;

(b) cooling the effluent from the first reaction zone to 150°-300° C., preferably 200°-300° C.; and (c) thereafter continuing the oxidative dehydrogenation downstream of the first reaction zone in a second reaction zone by introducing additional gaseous oxygen into the gaseous stream in an amount insufficient to raise the reactor temperature above 700° C.

In another aspect, the present invention provides an improved process for the preparation of alkyl glyoxylates by the reaction of a corresponding alkyl glycolate with oxygen or an oxygen-containing gas at a temperature of from about 400°-700° C. in the presence of a silver catalyst in at least two essentially adiabatic reaction stages in series.

In a preferred aspect of the present process, the alkyl glycolate is introduced with up to about 60 percent of the stoichiometric amount of oxygen at a reaction temperature of 150° to 300° C. into a first substantially adiabatic reaction stage. Additional oxygen is then mixed with the reaction mixture effluent from the first stage at a reaction temperature of 150° to 300° C. and then introduced into a second substantially adiabatic reaction stage, both reaction stages being at a temperature below 700° C.

DETAILED DESCRIPTION OF THE INVENTION

The preferred catalyst for the process of the present invention is silver. It is preferred to use an unsupported crystalline silver catalyst, which has the advantage of including a high space time yield and a high selectivity. Preferably, high purity silver, e.g., in the form of 99.99 percent pure crystals, is used. The preferred configuration of the catalyst particles is in a horizontal shallow fixed catalyst bed.

The oxidative dehydrogenation of alkyl glycolates liberates so much heat that, if not controlled, the temperature of the reaction mass is raised above the temperature at which decomposition of the reactants occur. The present invention is directed to a process of controlling the temperature of the reactions so as to avoid the decomposition of the reactants and products.

According to this invention, a high conversion to the alkyl glyoxylate is achieved with a high selectivity, as well as management of the liberated heat of reaction, by carrying out the reaction in two or more reaction stages in series and by providing in the first reaction stage less than the stoichiometric amount of oxygen theoretically required to completely oxidatively dehydrogenate all of the alkyl glycolate to the corresponding alkyl glyoxylate, preferably less than about 60 percent. The effluent from the reaction stages is cooled between stages to provide further temperature control and the product gaseous stream from the last reaction stage is cooled and condensed. In each reaction stage, there is either excess alkyl glycolate or previously formed alkyl glyoxylate product which, as a result of the intercooling, introduces the reaction mixture to a reactor at a temperature below the desired maximum to provide further heat-absorbing capacity to the system.

Although any number of reaction stages in series may be used, little additional benefit in temperature control or overall yield of product is obtained by the use of more than four reactors in series. Preferably, only two reaction stages in series are used.

It is important that the gaseous mixture fed to the first reactor is uniformly and completely mixed in the gaseous state to form a homogenous gaseous stream. Any one of a number of conventional means can be used to accomplish this. One preferred method is to vaporize the alkyl glycolate in a long vertical tube evaporator and provide a fiber bed downstream of the evaporator to remove any mist left in the mixture. Preferably, the air is preheated and then uniformly mixed with the heated alkyl glycolate at a temperature high enough to avoid the formation of any mist. Failure to eliminate the mist or entrained liquid may adversely affect the reaction selectivity and life of the catalyst.

The air or other source of gaseous oxygen may be preheated in a preheater, preferably to a temperature above the condensation temperature of the alkyl glycolate. The oxygen source is fed directly to the air preheater. It is preferred to use an overall amount of oxygen in the process of this invention of from 0.05 to 1.0, preferably from 0.4 to 0.8, moles of oxygen per mole of alkyl glycolate in the starting gaseous mixture entering the first reaction stage. If the oxygen source is mixed with previously vaporized alkyl glycolate, it is preferred to preheat the oxygen-containing gas to a temperature above the condensation point of alkyl glycolate in order to prevent the formation of mist during mixing.

Although no carrier gas need be used, it is preferred to add to the alkyl glycolate vaporizer from 1 to 3 moles of nitrogen per mole of alkyl glycolate, in addition to that present in the incoming air, to aid in vaporization and in temperature control inside the reactor. More nitrogen may optionally be added to control the reactor temperature.

The amount of oxygen entering the first stage with alkyl glycolate preferably is no more than about 60 percent of the stoichiometric amount, based on the alkyl glycolate entering the first stage, and is preferably from about 40 to 55 percent.

The gaseous reaction mixture, including the vaporized alkyl glycolate, oxygen, and optionally nitrogen, either that present in the air used as the source of oxygen alone or in admixture with from about 0 to 5, preferably 1 to 4 molar equivalents additional diluent nitrogen, entering the first reaction stage is preferably at a temperature of from about 200° to 300° C. As this gaseous reaction mixture passes through the catalyst bed, resulting in the liberation of heat, the temperature of the reaction mass increases. The mean temperature of the reaction mass in the catalyst bed in the first stage is preferably from about 400°-700° C., more preferably from about 450°-625° C. and in the second and any succeeding stages is preferably from about 400°-700° C., more preferably from about 450°-625° C. The effluent from the first reaction stage contains the alkyl glyoxylate product, unreacted alkyl glycolate, water vapor, alcohol, and nitrogen, if air is used as the source of oxygen or if nitrogen is used as a carrier gas.

Additional oxygen is added to the effluent from the first reactor after cooling the effluent, preferably to below 300° C. This procedure is employed for the reaction mixture leaving each non-final reaction stage. The amount of oxygen added to the reaction mixture as it leaves any of the non-final stages is dependent upon the cumulative amount introduced to the preceding stage or stages and upon the total number of reaction stages remaining. Preferably, sufficient oxygen is added at each of these inner stage points so that the total amount of oxygen that has been added to the system, including the amount added to the first reactor, is at least equal to and preferably slightly in excess, e.g., from 100% to 120%, of the stoichiometric requirement of oxygen based on the amount of alkyl glycolate in the feedstream.

For example, when two reaction stages are used, it is preferred to introduce from about 40 to 55 percent of the stoichiometric oxygen to the first stage and from about 60 to 45 percent or more of the stoichiometric amount thereof in the second stage, the total amount of oxygen fed to the system ordinarily being at least equal to 100 percent of the stoichiometric amount of oxygen needed to oxidatively dehydrogenate all of the alkyl glycolate feed.

Since alkyl glyoxylates form oligomers and other side reactions occur at elevated temperatures, it is preferred to rapidly cool the effluent from each of the reaction stages. This prevents undesirable decomposition of the product, as well as providing heat absorbing capacity for temperature control for the second and any succeeding reaction stages. The cooling, e.g., in a heat exchanger, between the reaction stages preferably is sufficient to cool the gaseous stream to a temperature below about 300° C., and more preferably to about 200° to 300° C.

If desired, the oxygen or oxygen-containing gases added between stages can be at a temperature sufficiently lower than the reaction effluent to which it is added in order to at least partially effect this interstage cooling. Alternatively or additionally, cooling in conventional heat exchange equipment, such as a standard shell and tube heat exchanger, can be used to cool the reaction mixture to the selected lower temperature before it is introduced into the next succeeding stage.

The heat liberated in each of the stages of this multistage process is controlled in the manner described herein to maintain the temperature in each of the reactors within the desired range. This is accomplished, at least in part, by supplying less than a stoichiometric equivalent amount of oxygen to the first stage, which results in the oxidation of only a portion of the alkyl glycolate, thereby reducing the amount of heat generated in the first stage. The unreacted alkyl glycolate also serves as a heat sink for heat liberated in the reaction, thereby assisting in preventing the reaction temperatures from rising above about 700° C. In the succeeding reaction stages, this heat absorbing capacity is provided by the alkyl glyoxylate product, water vapor, and alcohol produced by the oxidation reaction. Consequently, the present invention permits the substitution of less costly interstage cooling equipment in place of, for example, cooling equipment inside the reactor itself, or the use of large volumes of an inert carrier gas to act as a heat sink.

The rate of heat transfer through the walls of the reactor is not a critical variable in the process of this invention. Consequently, the reactor need not have a high surface area to volume ratio. In a preferred embodiment, the reactor walls are insulated. Each reaction stage is essentially adiabatic, that term being understood to mean that the reaction occurs without loss of heat of reaction from the reaction stage itself.

The absolute pressure of the gas mixture in the reactors, including inert gases, if any, is not critical and can be varied. It is preferred to operate the process at a pressure of from about 0.5 to 2.0 atmospheres.

The rate of conversion of an alkyl glycolate can be varied over a wide range, depending on the amount of excess oxygen utilized and the temperatures employed in the reaction stages. It is preferred to employ conditions whereby the conversion rate of the alkyl glycolate ranges from about 20-100 percent, more preferably about 75-95 percent. As the conversion declines below the preferred range, it becomes increasingly expensive to isolate the product. The reaction can be carried out in the presence of an inert gas, preferably nitrogen, which provides additional heat absorbing capacity. As the conversion rate approaches 100 percent, selectivity tends to drop.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

EXAMPLES

EXAMPLE 1

Methyl glycolate was vaporized at a rate of 0.251 mole/hr in a stream of nitrogen (0.33 mole/hr) and the resultant mixed with air (104 cubic centimeters/min at standard temperature and pressure containing 0.059 mole/hr oxygen and 0.223 mole/hr nitrogen). The combined gas stream was passed at a pressure approximately 1 atmosphere absolute into a quartz tube 20 cm in length × 10 millimeters inner diameter containing a cylindrical bed of crystalline silver (7.0 g) that was 2 cm deep and had been preheated to 425° C. An exothermic reaction ensued, causing the catalyst bed temperature to rise. To simulate adiabatic conditions in this small reactor, an external electric heater around the reactor was adjusted to compensate for the heat lost through the reactor walls to the surroundings, causing the catalyst bed temperature to stabilize at 530° C. The effluent gas from this reactor was mixed with additional air (140 cubic centimeters/min at standard temperature and pressure containing 0.079 mole/hr oxygen) and the combined gases cooled to 220° C. and passed into a second reactor identical to the first in all respects and preheated to 475° C. A second exothermic reaction ensued. An external electric heater around the second reactor was adjusted to compensate for heat lost through the reactor wall to the surroundings, causing the catalyst bed to stabilize at 550° C. The exit stream was cooled to 25° C., causing condensation of liquid products. Analysis of the liquid by gas chromatography revealed the presence of methyl glycolate (0.028 mole/hr) and methyl glyoxylate (0.145 mole/hr), corresponding to a conversion of 89 percent and selectivity of 65 percent.

Improvement in selectivity over prior art processes is also achieved by otherwise following the procedure of Example 1, except employing ethyl glycolate instead of methyl glycolate; introducing oxygen at more than two points in the gaseous stream.

EXAMPLE 2 (COMPARATIVE EXAMPLE)

Methyl glycolate (0.243 mole/hr) was vaporized in a stream of nitrogen (0.33 mole/hr) and the resultant mixed with air (245 cubic centimeters/min at standard temperature and pressure corresponding to 0.138 mole/hr oxygen and about 0.519 mole/hr nitrogen). The gas mixture was passed through a quartz tube 20 centimeters in length × 10 millimeters inner diameter containing silver crystals (7.0 g) that were in the form of a cylindrical bed 2 centimeters deep that had been preheated to 450°. An exothermic reaction ensued. An external electric heater surrounding the catalyst bed was adjusted so as to compensate for heat lost to the surroundings through the reactor wall. The catalyst stabilized at 630° C. The exit stream was cooled to 25° C., causing condensation of liquid products. Analysis of the liquid products by gas chromatography revealed the presence of methyl glycolate (0.028 mole/hr) and methyl glyoxylate (0.106 mole/hr) corresponding to a conversion of 89 percent and a selectivity of 49 percent.

The preceding examples can be repeated with similar success by substituting the generically or specifically described reactants and/or operation conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyzed gas phase oxidative dehydrogenation of an alkyl glycolate to an alkyl glyoxylate in which a continuous stream of a homogeneous gaseous mixture of the alkyl glycolate and oxygen-containing gas is contacted with a catalyst at a temperature effective to initiate the oxidative dehydrogenation, which comprises:
   (a) conducting the oxidative dehydrogenation initially in a first reaction zone in the presence of an amount of oxygen which is equal to or less than 60% of the stoichiometric amount and at a temperature of from about 400° C. up to a temperature which is below 700° C. as the upper limit;
   (b) cooling the effluent gas;
   (c) thereafter continuing the oxidative dehydrogenation downstream of the first reaction zone in a second reaction zone by introducing additional gaseous oxygen into the gaseous stream at a temperature of from about 400° C. up to a temperature which is below 700° C. as the upper limit such that the total amount of oxygen added to the system is at least a stoichiometric amount based on the glycolate reactant.

2. The process of claim 1, wherein the process is performed in two reaction stages in series in which about 40 to 55 percent of the stoichiometric amount of oxygen is introduced in the first stage and about 60 to 45 percent thereof in the second stage.

3. The process of claim 1, wherein the temperature of the first reaction stage is about 450°–625° C.

4. The process of claim 1, wherein the reactions are carried out at a pressure of from about 0.5 to 2.0 atmospheres.

5. The process of claim 1, wherein the process is conducted in the presence of an inert gas.

6. The process of claim 5, wherein the inert gas is nitrogen.

7. The process of claim 6, wherein the process is conducted in the presence of from 1 to 4 moles of nitrogen per mole of alkyl glycolate.

8. The process of claim 1, wherein the alkyl moiety of the alkyl glycolate and alkyl glyoxylate contains from 1 to 6 carbon atoms.

9. The process of claim 1, wherein the alkyl glycolate is methyl glycolate.

10. The process of claim 1, wherein the reaction effluent mixture obtained in step (b) is cooled prior to step (c) to below about 300° C.

11. The process of claim 10, wherein the reaction mixture effluent is cooled to about 200° to 300° C.

12. The process of claim 1, wherein the process is performed in two reaction stages in series and about 40 to 55 percent of the stoichiometric amount of oxygen is introduced in the first stage.

13. The process of claim 12, wherein the temperature of the second stage is about 450°–625° C.

14. In a process for the preparation of alkyl glyoxylates by reacting a corresponding alkyl glycolate with oxygen or an oxygen-containing gas at a temperature of from about 450°–625° C. in the presence of a metallic silver catalyst, the improvement which comprises performing the reaction in two essentially adiabatic reaction stages in series, which is characterized by:
   (a) introducing the alkyl glycolate and about 45 percent of the stoichiometric amount of oxygen to the first reaction stage at a temperature sufficiently low to maintain the temperature of the reaction in the first stage between 450°–625° C.,
   (b) cooling the effluent to below 300° C.,
   (c) introducing additional oxygen-containing gas into the reaction mixture effluent of the first stage such that the total amount of oxygen in the system is at least a stoichiometric amount based on the glycolate reactant, and
   (d) introducing the resultant reaction mixture of step (c) to the succeeding reaction stage at a temperature sufficiently low to maintain the temperature in the second stage between 450°–625° C.

15. The process of claim 14, wherein the alkyl glycolate is methyl glycolate.

16. The process of claim 14, wherein from 1 to 4 moles of nitrogen are used in the reactions per mole of alkyl glycolate.

17. The process of claim 14, wherein the reactions are carried out at a pressure of from about 0.5 to 2.0 atmospheres.

18. The process of claim 14, wherein the oxygen-containing gas is air.

19. The process of claim 1, wherein the oxygen-containing gas is air; wherein the alkyl glycolate is methyl glycolate; wherein the process is performed in two reaction stages and about 40 to 55 percent of the stoichiometric amount of oxygen is introduced in the first stage; wherein the reaction effluent mixture obtained in step (b) is cooled prior to step (c) to below about 300° C.; wherein the temperature of the first reaction stage is about 450°–625° C.; and wherein the temperature of the second stage is about 450°–625° C.

20. In a process for the preparation of an alkyl glyoxylate by reacting a corresponding alkyl glycolate with gaseous oxygen or an oxygen-containing gas at a temperature of from about 400°–700° C. in the presence of a silver catalyst, the improvement which comprises conducting the reaction in at least two essentially adiabatic reaction stages in series, which comprises the steps of:

(a) introducing at a temperature of 150° to 300° C. to about 60 percent of the stoichiometric amount of the oxygen into a first reaction stage;
(b) cooling the effluent to below 300° C.;
(c) introducing an additional amount of oxygen into the gaseous reaction mixture effluent from the first stage such that the total amount of oxygen in the system is at least a stoichiometric amount based on the glycolate reactant; and
(d) introducing the resultant gaseous mixture at a temperature of 150° to 300° C. from step (c) into a succeeding reaction stage.

21. The process of claim 20, wherein the oxygen-containing gas is air; wherein the alkyl glycolate is methyl glycolate; wherein the process is performed in two reaction stages and about 40 to 55 percent of the stoichiometric amount of oxygen is introduced in the first stage; wherein the reaction effluent mixture obtained in step (b) is cooled prior to step (c) to below about 300° C.; wherein the temperature of the first reaction stage is about 450°–625° C.; and wherein the temperature of the second stage is about 450°–625° C.

* * * * *